United States Patent
Jeong et al.

(10) Patent No.: US 10,768,137 B2
(45) Date of Patent: Sep. 8, 2020

(54) GAS DETECTING SENSOR

(71) Applicants: LG Chem, Ltd., Seoul (KR); Korea University Research and Business Foundation, Seoul (KR)

(72) Inventors: Kwang Seob Jeong, Seoul (KR); Hang Beum Shin, Daejeon (KR); Dong Sun Choi, Gyeonggi-do (KR); Bit Na Yoon, Seoul (KR); Ju Yeon Jeong, Gyeonggi-do (KR)

(73) Assignees: LG Chem, Ltd. (KR); Korea University Research and Business Foundation (KR)

( * ) Notice: Subject to any disclaimer, the term of this patent is extended or adjusted under 35 U.S.C. 154(b) by 0 days.

(21) Appl. No.: 16/346,592

(22) PCT Filed: Nov. 2, 2017

(86) PCT No.: PCT/KR2017/012334
§ 371 (c)(1),
(2) Date: May 1, 2019

(87) PCT Pub. No.: WO2018/084602
PCT Pub. Date: May 11, 2018

(65) Prior Publication Data
US 2019/0257784 A1 Aug. 22, 2019

(30) Foreign Application Priority Data

Nov. 2, 2016 (KR) .......... 10-2016-0144843
Nov. 2, 2017 (KR) .......... 10-2017-0145147

(51) Int. Cl.
G01N 27/41 (2006.01)
G01N 33/00 (2006.01)
G01N 27/414 (2006.01)

(52) U.S. Cl.
CPC ..... G01N 27/4141 (2013.01); G01N 27/4146 (2013.01); G01N 33/004 (2013.01)

(58) Field of Classification Search
CPC .......... G01N 27/4141; G01N 27/4146; G01N 33/004
See application file for complete search history.

(56) References Cited

U.S. PATENT DOCUMENTS 9,368,667 B1 * 6/2016 Kim .................. H01L 31/02327
9,825,154 B2 * 11/2017 Yap ....................... H01L 29/775
(Continued)

FOREIGN PATENT DOCUMENTS

EP 3163296 A1 5/2017
JP 2007529747 A 10/2007
(Continued)

OTHER PUBLICATIONS

International Search Report dated Feb. 13, 2018 in PCT/KR2017/012334, 4 pages.
(Continued)

Primary Examiner — Ida M Soward
(74) Attorney, Agent, or Firm — Lerner, David, Littenberg, Krumholz & Mentlik, LLP

(57) ABSTRACT

A gas detecting sensor including a substrate, a gate electrode provided on the substrate, an insulating layer provided on the gate electrode, a source electrode and a drain electrode, provided on the insulating layer, respectively, an n-type channel provided between the source electrode and the drain electrode, and a quantum dot layer provided on the n-type channel and provided so as to have electronic transition energy capable of resonating with vibration energy of a target gas molecule.

8 Claims, 3 Drawing Sheets

(56) References Cited

U.S. PATENT DOCUMENTS

| | | | |
|---|---|---|---|
| 2002/0117659 A1 | 8/2002 | Lieber et al. | |
| 2009/0008628 A1* | 1/2009 | Choi | B82Y 20/00 257/13 |
| 2009/0124052 A1* | 5/2009 | Chen | B82Y 10/00 438/158 |
| 2010/0019226 A1* | 1/2010 | Kahya | B82Y 10/00 257/24 |
| 2010/0135854 A1* | 6/2010 | Yang | G01N 33/54346 422/68.1 |
| 2012/0012817 A1* | 1/2012 | Hong | B82Y 10/00 257/29 |
| 2012/0096928 A1* | 4/2012 | Occhipinti | G01N 27/4141 73/31.06 |
| 2013/0032784 A1* | 2/2013 | Chaji | H01L 29/0673 257/27 |
| 2014/0034944 A1* | 2/2014 | Zan | H01L 29/7869 257/43 |
| 2014/0197405 A1* | 7/2014 | Vellaisamy | H01L 29/66969 257/43 |
| 2014/0361304 A1* | 12/2014 | Cho | H01L 29/1033 257/66 |
| 2016/0123947 A1* | 5/2016 | Briman | G01N 27/127 422/90 |
| 2016/0285020 A1* | 9/2016 | Huang | H01L 51/428 |
| 2017/0005281 A1* | 1/2017 | Afzali-Ardakani | H01L 29/127 |
| 2017/0154905 A1* | 6/2017 | Yuan | C23C 14/5853 |
| 2018/0315883 A1* | 11/2018 | Bessonov | A61B 5/02433 |
| 2019/0173428 A1* | 6/2019 | Kiehl | H01F 10/329 |

FOREIGN PATENT DOCUMENTS

| | | |
|---|---|---|
| JP | 200942232 A | 2/2009 |
| JP | 2009229341 A | 10/2009 |
| KR | 20030055346 A | 7/2003 |
| KR | 20150072888 A | 6/2015 |
| KR | 101616560 B1 | 4/2016 |
| KR | 20160071001 A | 6/2016 |

OTHER PUBLICATIONS

Extended European Search Report for EP17866955 dated Sep. 17, 2019, 9 pages.

Liu, et al., "Physically Flexible, Rapid-Response Gas Sensor Based on Colloidal Quantum Dot Solids," Advanced Materials, May 7, 2014, pp. 2718-2724, vol. 26, Issue 17.

Zan, et al., Room-temperature-operated sensitive hybrid gas sensor based on amorphous indium gallium zinc oxide thin-film transistors, Applied Physics Letters, Jun. 22, 2011, pp. 253503-1-253503-3, vol. 98, No. 25.

Liu H, Li M, Voznyy O, Hu L, Fu Q, Zhou D, Xia Z, Sargent EH, Tang J. Physically flexible, rapid-response gas sensor based on colloidal quantum dot solids. Advanced Materials. May 2014;26(17):2718-24.

Liu H, Li M, Shao G, Zhang W, Wang W, Song H, Cao H, Ma W, Tang J. Enhancement of hydrogen sulfide gas sensing of PbS colloidal quantum dots by remote doping through ligand exchange. Sensors and Actuators B: Chemical. Jun. 1, 2015;212:434-9.

* cited by examiner

GAS DETECTING SENSOR

CROSS-REFERENCE TO RELATED APPLICATIONS

The present application is a national phase entry under 35 U.S.C. § 371 of International Application No. PCT/KR2017/012334, filed Nov. 2, 2017, published in Korean, which claims priority from Korean Patent Application No. 10-2016-0144843 filed on Nov. 2, 2016, and Korean Patent Application No. 10-2017-0145147 filed on Nov. 2, 2017, all of which are incorporated herein by reference.

TECHNICAL FIELD

The present invention relates to a gas detecting sensor, and particularly, relates to a gas detecting sensor using quantum dots.

BACKGROUND ART

As quantum dots control their size, they can easily control energy bandgaps, thereby being used as a light emitting material by using such characteristics. In addition, the quantum dots can generate electric charges by absorbing light of various wavelengths, and thus can be utilized as a material for a gas detecting sensor and a light detecting sensor in addition to the light emitting material.

Conventionally, a non-dispersive infrared (NDIR) sensor is used to measure a concentration of carbon dioxide, but for a real-time measurement, it has an inefficient aspect because of high energy consumption and long warm-up time of the equipment.

DISCLOSURE

Technical Problem

It is a problem to be solved by the present invention to provide a gas detecting sensor capable of measuring a current change of a quantum dot layer according to resonance of in-band electronic transition energy of a quantum dot layer and a target gas molecule.

Technical Solution

To solve the above-described problem, according to one aspect of the present invention, there is provided a gas detecting sensor comprising a substrate, a gate electrode provided on the substrate, an insulating layer provided on the gate electrode, a source electrode and a drain electrode, provided on the insulating layer, respectively, an n-type channel provided between the source electrode and the drain electrode, and a quantum dot layer provided on the n-type channel and provided so as to have electronic transition energy capable of resonating with vibration energy of a target gas molecule.

In addition, according to another aspect of the present invention, there is provided a gas detecting sensor comprising a substrate, a gate electrode provided on the substrate, an insulating layer provided on the gate electrode, a source electrode and a drain electrode, provided on the insulating layer, respectively, and a quantum dot layer provided so as to electrically connect the source electrode and the drain electrode and provided so as to have electronic transition energy capable of resonating with vibration energy of a target gas molecule.

Advantageous Effects

As described above, according to the gas detecting sensor according to at least one example of the present invention, it can measure the current change of the quantum dot layer according to the resonance between the electronic transition energy of the quantum dot layer and the vibration energy of the target gas molecule, thereby measuring the target gas concentration.

DETAILED DESCRIPTION

Figure 1:
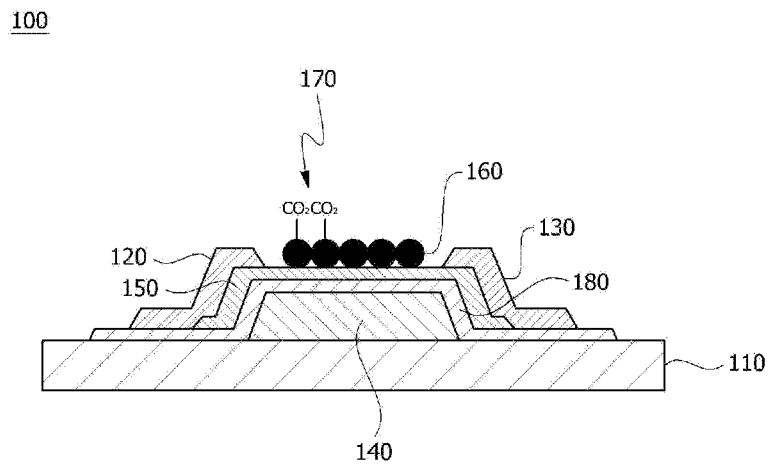
FIG. 1 is a schematic sectional view showing a gas detecting sensor according to a first example of the present invention.

Hereinafter, a gas detecting sensor according to one example of the present invention will be described in detail with reference to the accompanying drawings.

In addition, the same or similar reference numerals are given to the same or corresponding components regardless of reference numerals, of which redundant explanations will be omitted, and for convenience of explanation, the size and shape of each constituent member as shown may be exaggerated or reduced.

Figure 2:
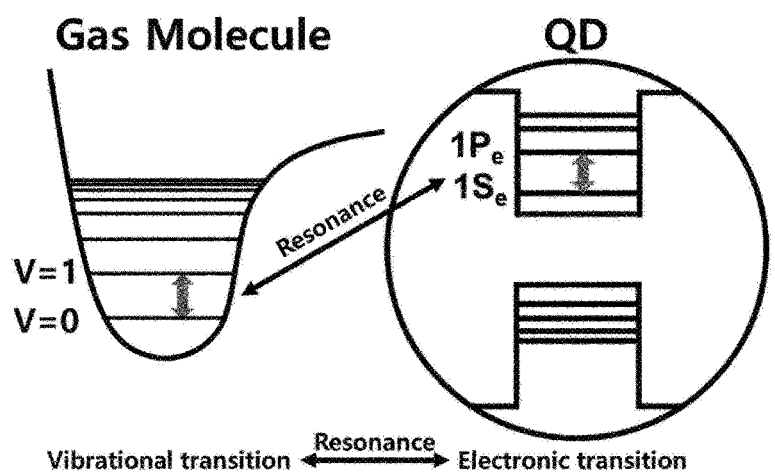
FIG. 2 is a conceptual diagram for explaining resonance of in-band electronic transition energy of a quantum dot layer and vibration energy of a target gas molecule.
Figure 3:
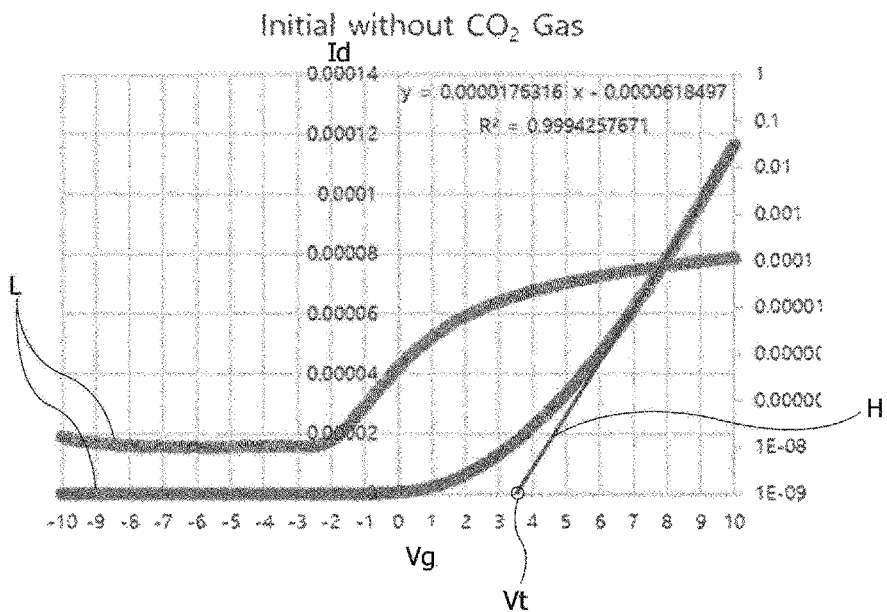
FIGS. 3 to 5 are graphs showing experimental results using the gas detecting sensor of the present invention.

FIG. 1 is a schematic sectional view showing a gas detecting sensor (100) according to a first example of the present invention, FIG. 2 is a conceptual diagram for explaining resonance of in-band electronic transition energy of a quantum dot layer and vibration energy of a target gas molecule, and FIG. 3 is a graph showing experimental results using the gas detecting sensor of the present invention.

The present invention provides a gas detecting sensor (100) comprising a quantum dot layer (160) formed on an n-type channel. Also, the quantum dot layer (160) is provided so as to have electronic transition energy capable of resonating with vibration energy of a target gas (e.g., carbon dioxide) molecule (170).

Also, by controlling the in-band electronic transition energy of the quantum dot layer (160), the gas detecting sensor (100) can be used for various gas concentration measurements.

Furthermore, it can induce a fine potential difference to a current change and measure it, wherein the potential difference is generated when the potential of a quantum dot layer is changed according to electronic-vibrational energy transfer between the quantum dot layer (160) and a target gas molecule.

Referring to FIG. 1, the gas detecting sensor (100) related to the first example comprises a substrate (110), a gate electrode (140), an insulating layer (180), a source electrode (120), a drain electrode (130), an n-type channel (150), and a quantum dot layer (160).

Specifically, the gas detecting sensor (100) related to one example of the present invention comprises a substrate (110), a gate electrode (140) provided on the substrate (110), an insulating layer (180) provided on the gate electrode (140), and a source electrode (120) and a drain electrode (130), provided on the insulating layer (180), respectively. Also, the gas detecting sensor (100) comprises an n-type channel (150) provided between the source electrode (120) and the drain electrode (130) and a quantum dot layer (160) provided so that the current flows and provided on the n-type channel (150). Furthermore, the source electrode (120) and the drain electrode (130) are provided over the insulating layer (180) and the n-type channel (150), respectively.

Also, the n-type channel (150) is provided to electrically connect the source electrode (120) and the drain electrode (130).

The quantum dot layer (160) is provided so as to have the electronic transition energy (in-band electronic transition energy) capable of resonating with the vibration energy of the target gas molecule.

In addition, the quantum dot layer (160) may also be provided to electrically connect the source electrode (120) and the drain electrode (130) and the quantum dot layer (160) may also be provided so as not to electrically connect the source electrode (120) and the drain electrode (130).

The quantum dot layer (160) is one arranged such that a number of quantum dots having a spherical shape form a layer, where the quantum dots can easily control an energy gap of an electron structure by controlling the size and composition thereof.

The operation principle of the gas detecting sensor (100) using the quantum dots is to detect the current flowing in the quantum dot layer (160) in real time and to use the current change of the quantum dot layer (160). For example, in the case of the gas detecting sensor (100) using the quantum dots, it is combined with a field-effect thin film transistor (TFT), which can be utilized.

Also, the quantum dot layer (160) may be formed in a film form.

In the field-effect thin film transistor, the current change of the quantum dot layer (160) causes its electrons to move to the conduction channel of the n-type channel (150) to generate a change in the threshold voltage, which can be measured and applied as the biosensor. Specifically, in the field-effect thin film transistor, the change of the functional group occurring on the surface of the quantum dot layer (16) changes the potential of the quantum dots, where electrons convert this fine potential change into the current change of a conduction channel of the n-type channel to amplify it. In summary, the change of the surface potential at the quantum dots indicates the current change in the thin film transistor soon and also appears as a change in threshold voltage, which can be measured and applied as the gas detecting sensor (100).

Specifically, when a voltage equal to or higher than the threshold voltage is applied between the source electrode (120) and the gate electrode (140) in the TFT, a conduction channel is formed in the n-type channel, through which electrons can move between the source electrode (120) and the drain electrode (130). And, the potential of the quantum dots may also affect the n-type conduction channel, thereby affecting the threshold voltage.

Referring to FIG. 2, the gas detecting sensor (100) according to the present invention can observe the potential difference induced in the quantum dot layer (160) when the current is measured in real time between the source electrode (120) and the gate electrode (130), which is provided so as to measure the current changed according to the specific electronic-vibrational energy transfer transferred from the target gas molecules to the quantum dot layer (160) (QD). In addition, the current to be measured causes the current change, as the in-band transition energy of the quantum dots is absorbed by vibration of the specific functional group of the target gas molecule.

Also, the increase of the potential by the vibration of the target gas molecule is a new and highly feasible measurement method, where the potential value is proportional to the concentration of the biomolecules.

Furthermore, since the energy transfer is by coupling between the quantum dot layer (160) and the gas molecule vibration, information on the physical distance between the gas molecule and the quantum dot layer (160) can also be measured.

Besides, the usable n-type channel (150) in the present invention may include any one of n-type materials selected from the group consisting of IGZO, ZnO, ZTO, IZO, IHZO, AlN, InN, GaN and InGaN.

In particular, an n-type channel (15) including IGZO is preferred, because it has excellent optical transparency, amorphous structure and high electron mobility, and quantum dots can also be directly functionalized on the IGZO channel. Furthermore, the IGZO channel can directly function as an active matrix backplane, which has an advantage that a separate integration process can be omitted.

Also, it is preferred that as the usable quantum dots in the present invention, colloidal quantum dots are used. When the colloidal quantum dots are used, they can be formed by a simple method such as spin coating on the n-type channel (15), and the quantum dots can be uniformly distributed.

The quantum dots of the quantum dot layer (160) comprise a semiconductor compound of Group II-VI, a semiconductor compound of Group III-V, a semiconductor compound of Group IV-VI, a semiconductor compound of Group IV or a combination thereof.

Specifically, as the quantum dots, any one or more selected from the group consisting of AuS, AuSe, AuTe, AgS, AgSe, AgTe, AgO, CuS, CuSe, CuTe, CuO, CdS, CdSe, CdTe, ZnS, ZnSe, ZnTe, ZnO, HgS, HgSe, HgTe, AuSeS, AuSeTe, AuSTe, AgSeS, AgSeTe, AgSTe, CuSeS, CuSeTe, CuSTe, CdSeS, CdSeTe, CdSTe, ZnSeS, ZnSeTe, ZnSTe, HgSeS, HgSeTe, HgSTe, AuAgS, AuAgSe, AuAgTe, AuCuS, AuCuSe, AuCuTe, AuZnS, AuZnSe, AuZnTe, AuCdS, AuCdSe, AuCdTe, AuHgS, AuHgSe, AuHgTe, AgZnS, AgZnSe, AgZnTe, AgCuS, AgCuSe, AgCuTe, AgCdS, AgCdSe, AgCdTe, AgHgS, AgHgSe, AgHgTe, CuZnS, CuZnSe, CuZnTe, CuCdS, CuCdSe, CuCdTe, CuHgS, CuHgSe, CuHgTe, ZnCdS, ZnCdSe, ZnCdTe, ZnHgS, ZnHgSe, ZnHgTe, CdHgS, CdHgSe, CdHgTe, CdHgZnTe, CdZnSeS, CdZnSeTe, CdZnSTe, CdHgSeS, CdHgSeTe, CdHgSTe, HgZnSeS, HgZnSeTe, HgZnSTe; GaN, GaP, GaAs, GaSb, InN, InP, InAs, InSb, GaNP, GaNAs, GaNSb, GaPAs, GaPSb, InNP, InNAs, InNSb, InPAs, InPSb, GaInNP, GaInNAs, GaInNSb, GaIn-PAs, GaInPSb, SnS, SnSe, SnTe, PbS, PbSe, PbTe, SnSeS, SnSeTe, SnSTe, PbSeS, PbSeTe, PbSTe, SnPbS, SnPbSe, SnPbTe, SnPbSSe, SnPbSeTe, SnPbSTe, Si, Ge, SiC and SiGe can be used.

Particularly, the gas detecting sensor (100) related to one example of the present invention can use the quantum dot layer (160) having electronic transition in the infrared region, especially the mid-infrared region. In this case, quantum dots capable of absorbing light in the infrared region, particularly a wavelength of 1000 nm to 20 μm and preferably a wavelength of 1000 nm to 8000 nm, can be used by adjusting the type or size of the quantum dots. Also, since the colloidal quantum dots can be processed in a large area at low cost, it is preferred to use the colloidal quantum dots in the present invention.

In addition, as the quantum dots, ligand-substituted quantum dots can be used. The quantum dots may be substituted with at least one ligand of an organic ligand and an inorganic ligand. An example of a ligand may include EDT (ethanedithol), BDT (butanethiol), MPA (mercaptocarboxylic acid), CTAB (Cetyltrimethylammonium bromide), HTAC (hexadecyltrimethylammonium chloride), TBAI (tetrabutylammonium iodide) or $Na_2S$.

The quantum dots have a structure surrounded by an oleic acid ligand for dispersion and stability of the colloidal solution. The quantum dots in this state can also be applied to the gas detecting sensor, but since the oleic acid ligand has a long chain structure, electrons generated in the quantum dots are disturbed to move to the n-type channel (150). Therefore, it is preferred to substitute the ligand with a ligand having a shorter chain structure. When the ligand-substituted quantum dots are used, for example, a method may be used, in which the ligand is substituted by forming the quantum dots surrounded by the oleic acid ligand on the n-type channel (150) and then reacting them with the ligand.

Alternatively, the organic material ligand of the colloidal quantum dot layer may be substituted with a monomolecular organic ligand or inorganic ligand to improve accessibility of the target biomolecule and to facilitate resonance of the vibration mode of the functional group in the biomolecule and the in-band transition of the quantum dot layer.

In one example, a bidentate ligand such as EDT, BDT or MPA as described above will be used as the organic ligand for electric charge transfer, which may be mixed with an inorganic ligand to form the film structure of the colloidal quantum dot layer uniformly.

After synthesizing them using a compound providing halogen ions such as CTAB (Cetyltrimethylammonium bromide), CTACL (Cetyltrimethylammonium chloride) and TBAI (Tributylammonium iodide), the used organic ligands may be substituted with halogen ions such as $Br^-$, $Cl^-$ or $I^-$. The substitution process can be performed at room temperature by allowing the halogen ions to exist on the film composed of the colloidal quantum dot layer surrounded by the organic ligands for a few minutes. The thickness of the film can be increased sequentially, and the thickness can be from 10 nm to 300 nm. Because the halogen is an atomic ligand, it has no vibration motion by the ligand, so that it may remove a molecule to cause resonance phenomenon with the target gas molecule in the mid-infrared region. Accordingly, it is possible to obtain more improved and stable electric signals.

As another method for substituting it with inorganic ligands, a method using a polarity difference between a polar solution and a non-polar solution may be used. When the colloidal quantum dot solution modified with non-polar organic ligands is stirred with the polar inorganic ligand solution at room temperature, the polar ligands are modified on the surface of the colloidal quantum dots and the dielectric constant of the colloidal quantum dots is increased. Thus, colloidal quantum dots modified with the inorganic ligands are present in the polar solution. The colloidal quantum dot solution modified with the polar inorganic ligands has an advantage that the colloidal solution can be coated on the surface.

The insulating layer (180) may also be formed of $SiO2$, $Al2O3$, $TiO2$, $ZrO2$, $HfO2$ or $SiNx$, and the like.

Also, the gate electrode (140) may be formed of a metal, which may be, for example, selected from the group consisting of Cr, Mo, Al, Ti/Au, Ag, Cu and Pt.

Furthermore, the source electrode (120) and the drain electrode (130) may be each formed of a metal, which may be, for example, selected from the group consisting of Cr, Ti/Au, Mo, Al, Ag, Cu, Pt and W.

Besides, the remaining structures other than the insulating layer (180), the n-type channel (150), the quantum dot layer (160), and the source electrode and drain electrode (120, 130), as described above, are not particularly limited as long as they can be usually used in the gas detecting sensor (100).

For example, as the substrate (110), a glass substrate or a plastic substrate may be used.

Figure 4:
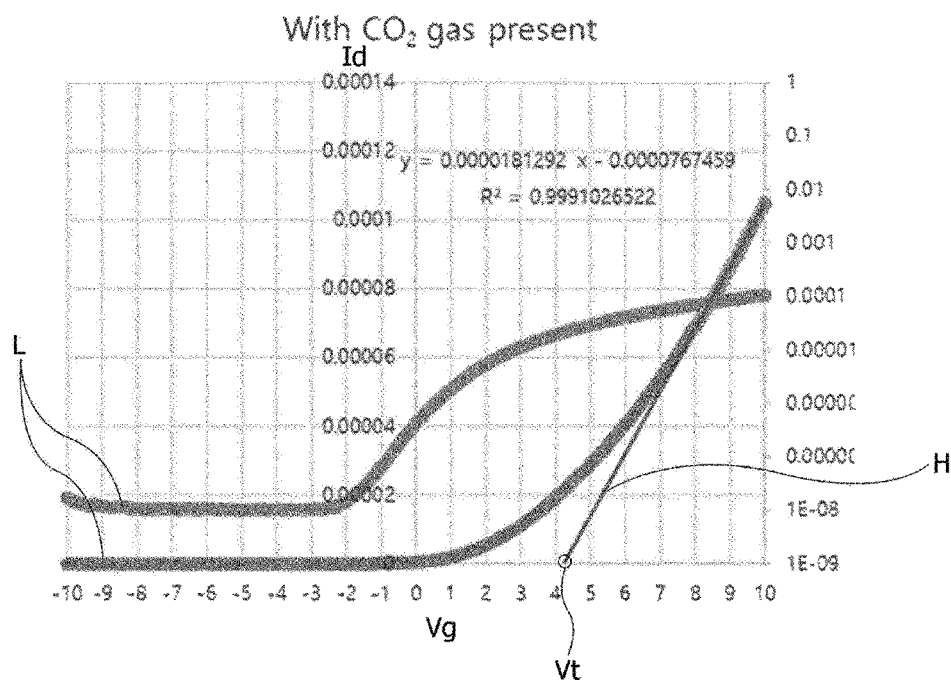
Figure 5:
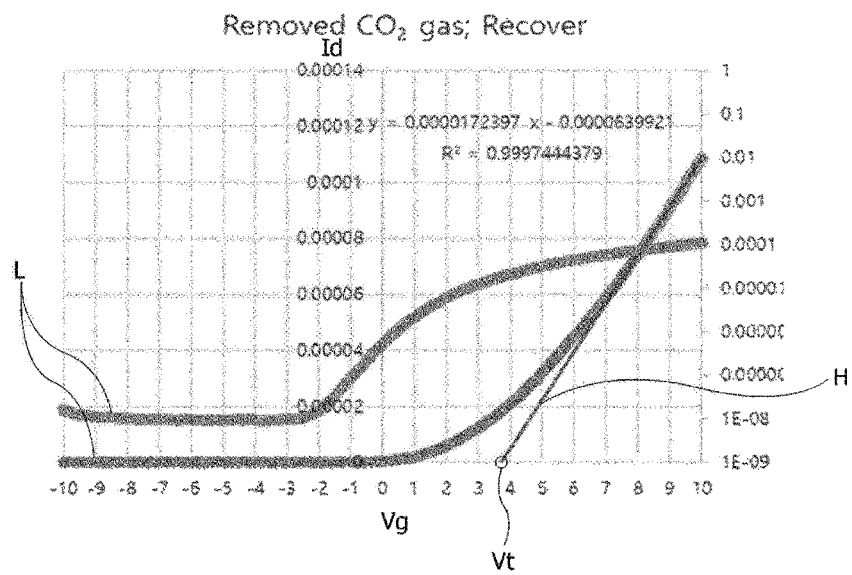

Referring to FIGS. 3 to 5, in the gas detecting sensor (100) shown in FIG. 1, a colloidal quantum dot film having a predetermined transition energy was coated on an n-type channel to measure variation of the current values due to the carbon dioxide gas while measuring Id (drain current)-Vg (gate voltage) of the gas detecting sensor. The quantum dot layer (160) was spin-coated to a thickness of 200 to 300 nm, and the sweeping range of the gate voltage Vg of the gas detecting sensor was set from –10 V to 10 V. A gas detecting system was constructed through the variation of the drain current or the variation of the threshold voltage (Vt) in the Id-Vg characteristic curve due to the energy resonance between the quantum dot layer and the carbon dioxide gas.

Referring to FIGS. 3 to 5, it can be confirmed that the threshold voltage (Vt) of the gas detecting sensor has been shifted due to the presence of carbon dioxide gas. Also, it can be confirmed that when the carbon dioxide gas is removed, the threshold voltage (Vt) returns. This is because the potential change changed by adsorbing the carbon dioxide on the quantum dot layer or the electrical coupling force in the chemical adsorption of the surface of the quantum dot layer affects the electric field on the n-type channel (150) in which the current flows under the quantum dot layer, whereby it can be confirmed that it affects the threshold voltage (Vt).

Referring to FIG. 3 which is the initial state, it can be confirmed that the threshold voltage (Vt), which is an intersection line between the straight line (H) and the x-axis (Vg), is formed at 4 V or less.

Also, referring to FIG. 4, it can be confirmed that when the adsorption of carbon dioxide occurs, the threshold voltage (Vt) is changed to 4V or more.

Furthermore, referring to FIG. 5, when the carbon dioxide is removed, it can be confirmed that the threshold voltage (Vt) returns to 4 V or less, whereby it can be seen that the reaction with the carbon dioxide occurs in the quantum dot layer (160).

Lines (L1) and (L2) in FIGS. 3, 4 and 5 represents graphs in which the drain current (Id) is expressed on a log scale and a square root scale, respectively.

Figure 6:
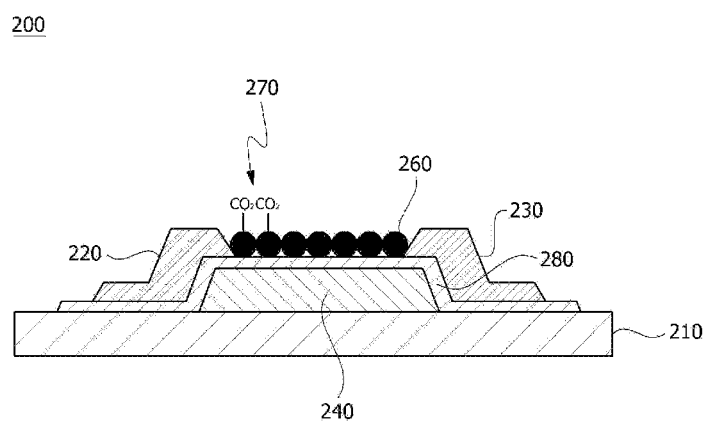
FIG. 6 is a schematic sectional view showing a gas detecting sensor according to a second example of the present invention.

FIG. 6 is a schematic sectional view showing a gas detecting sensor (200) related to a second example of the present invention.

Referring to FIG. 6, the gas detecting sensor (200) comprises a substrate (210), a gate electrode (240) provided on the substrate (210), an insulating layer (280) provided on the gate electrode (240), and a source electrode (220) and a drain electrode (230), provided on the insulating layer (280), respectively. Also, the gas detecting sensor (200) comprises a quantum dot layer (260) positioned on the insulating layer (280), provided so that the current flows between the source electrode (220) and the drain electrode (230), and provided so as to have electronic transition energy capable of resonating with vibration energy of a target gas molecule.

In the second example, unlike the first example, the n-type channel layer (150) may not be provided and the quantum dot layer (260) electrically connects the source electrode (220) and the drain electrode (230).

The preferred examples of the present invention as described above are disclosed for illustrative purposes, which can be modified, changed and added within thought and scope of the present invention by those skilled in the art and it will be considered that such modification, change and addition fall within the following claims.

INDUSTRIAL APPLICABILITY

According to the gas detecting sensor related to at least one example of the present invention, it can measure the current change of the quantum dot layer depending on the resonance the electronic transition energy of the quantum dot layer and the vibration energy of the target gas molecule, thereby measuring the target gas concentration.

The invention claimed is:

1. A gas detecting sensor comprising:
    a substrate;
    a gate electrode provided on the substrate;
    an insulating layer provided on the gate electrode;
    a source electrode and a drain electrode, provided on the insulating layer, respectively;
    an n-type channel provided between the source electrode and the drain electrode; and
    a quantum dot layer provided on the n-type channel and provided so as to have electronic transition energy capable of resonating with vibration energy of a target gas molecule.

2. The gas detecting sensor according to claim 1, wherein the quantum dot layer comprises colloidal quantum dots.

3. The gas detecting sensor according to claim 1, wherein the quantum dot layer comprises a semiconductor compound of Group II-VI, a semiconductor compound of Group III-V, a semiconductor compound of Group IV-VI, a semiconductor compound of Group IV or a combination thereof.

4. The gas detecting sensor according to claim 3, wherein the quantum dot layer comprises one or more compounds selected from the group consisting of AuS, AuSe, AuTe, AgS, AgSe, AgTe, AgO, CuS, CuSe, CuTe, CuO, CdS, CdSe, CdTe, ZnS, ZnSe, ZnTe, ZnO, HgS, HgSe, HgTe, AuSeS, AuSeTe, AuSTe, AgSeS, AgSeTe, AgSTe, CuSeS, CuSeTe, CuSTe, CdSeS, CdSeTe, CdSTe, ZnSeS, ZnSeTe, ZnSTe, HgSeS, HgSeTe, HgSTe, AuAgS, AuAgSe, AuAgTe, AuCuS, AuCuSe, AuCuTe, AuZnS, AuZnSe, AuZnTe, AuCdS, AuCdSe, AuCdTe, AuHgS, AuHgSe, AuHgTe, AgZnS, AgZnSe, AgZnTe, AgCuS, AgCuSe, AgCuTe, AgCdS, AgCdSe, AgCdTe, AgHgS, AgHgSe, AgHgTe, CuZnS, CuZnSe, CuZnTe, CuCdS, CuCdSe, CuCdTe, CuHgS, CuHgSe, CuHgTe, ZnCdS, ZnCdSe, ZnCdTe, ZnHgS, ZnHgSe, ZnHgTe, CdHgS, CdHgSe, CdHgTe, CdHgZnTe, CdZnSeS, CdZnSeTe, CdZnSTe, CdHgSeS, CdHgSeTe, CdHgSTe, HgZnSeS, HgZnSeTe, HgZnSTe; GaN, GaP, GaAs, GaSb, InN, InP, InAs, InSb, GaNP, GaNAs, GaNSb, GaPAs, GaPSb, InNP, InNAs, InNSb, InPAs, InPSb, GaInNP, GaInNAs, GaInNSb, GaInPAs, GaInPSb, SnS, SnSe, SnTe, PbS, PbSe, PbTe, SnSeS, SnSeTe, SnSTe, PbSeS, PbSeTe, PbSTe, SnPbS, SnPbSe, SnPbTe, SnPbSSe, SnPbSeTe, SnPbSTe, Si, Ge, SiC and SiGe.

5. The gas detecting sensor according to claim 1, wherein the quantum dot layer comprises ligand-substituted quantum dots.

6. The gas detecting sensor according to claim 5, wherein the ligand-substituted quantum dots are substituted with at least one of an organic ligand or an inorganic ligand.

7. The gas detecting sensor according to claim 1, wherein the n-type channel is an n-type material selected from the group consisting of IGZO, ZnO, ZTO, IZO, IHZO, AlN, InN, GaN and InGaN.

8. A gas detecting sensor comprising:
    a substrate;
    a gate electrode provided on the substrate;
    an insulating layer provided on the gate electrode;
    a source electrode and a drain electrode, provided on the insulating layer, respectively; and
    a quantum dot layer provided on the insulating layer, provided so as to electrically connect the source electrode and the drain electrode, and provided so as to have electronic transition energy capable of resonating with vibration energy of a target gas molecule.

* * * * *